United States Patent
Brooks et al.

(10) Patent No.: US 11,918,443 B2
(45) Date of Patent: Mar. 5, 2024

(54) APPARATUS FOR FORMING A CATAMENIAL TAMPON

(71) Applicant: Johnson & Johnson GmbH, Neuss (DE)

(72) Inventors: Nick Brooks, Warwick (GB); Peter Morgan, Warwickshire (GB); James Stembridge, Warwickshire (GB); Trevor Whales, Warwickshire (GB)

(73) Assignee: Johnson & Johnson GmbH, Neuss (DE)

( * ) Notice: Subject to any disclaimer, the term of this patent is extended or adjusted under 35 U.S.C. 154(b) by 534 days.

(21) Appl. No.: 17/022,298

(22) Filed: Sep. 16, 2020

(65) Prior Publication Data

US 2021/0093488 A1 Apr. 1, 2021

Related U.S. Application Data

(60) Provisional application No. 62/907,190, filed on Sep. 27, 2019.

(51) Int. Cl.
| | |
|---|---|
| *B30B 11/04* | (2006.01) |
| *A61F 13/20* | (2006.01) |
| *B30B 11/00* | (2006.01) |
| *B30B 15/34* | (2006.01) |

(52) U.S. Cl.
CPC ........ *A61F 13/2088* (2013.01); *B30B 11/007* (2013.01); *B30B 11/04* (2013.01); *B30B 15/34* (2013.01)

(58) Field of Classification Search
CPC .............. A61F 13/2082; A61F 13/2091; A61F 13/2088; A61F 13/2085; B30B 7/04; B30B 11/007; B29C 43/02; B29C 43/021
See application file for complete search history.

(56) References Cited

U.S. PATENT DOCUMENTS

| | | |
|---|---|---|
| 3,854,481 A | 12/1974 | Messing |
| 4,212,301 A | 7/1980 | Johnson |
| 4,326,527 A | 4/1982 | Wollangk et al. |
| 4,627,849 A | 12/1986 | Walton et al. |
| 4,778,374 A | 10/1988 | Takahashi et al. |
| 5,153,971 A | 10/1992 | Van Iten |
| 5,370,633 A | 12/1994 | Villalta |
| 5,659,934 A | 8/1997 | Jessup et al. |
| 6,310,269 B1 | 10/2001 | Friese et al. |
| 7,120,977 B2 | 10/2006 | Bittner et al. |
| 7,736,572 B2 | 6/2010 | Gilbert et al. |
| 7,740,787 B2 | 6/2010 | Hubbard, Jr. et al. |
| 7,867,209 B2 | 1/2011 | Jorgensen et al. |
| 7,981,347 B2 | 7/2011 | Hubbard, Jr. et al. |
| 8,082,639 B2 | 12/2011 | Rolli |

(Continued)

FOREIGN PATENT DOCUMENTS

| | | |
|---|---|---|
| EP | 1459720 A | 9/2004 |
| EP | 1459720 B | 4/2005 |

(Continued)

OTHER PUBLICATIONS

International search report and written opinion dated Dec. 15, 2020, for International application PCT/EP2020/076950.

*Primary Examiner* — Thu Khanh T. Nguyen

(57) ABSTRACT

A doming tool for manufacturing absorbent tampon includes a plurality of stations made of devices for shaping a tampon pledget tip, and a hollow mandrel engaging with the stations. The stations are supported by at least one mounting plate.

8 Claims, 15 Drawing Sheets

(56) References Cited

U.S. PATENT DOCUMENTS

| | | |
|---|---|---|
| 8,293,968 B2 | 10/2012 | Schmidt-Först et al. |
| 8,460,262 B2 | 6/2013 | Fung et al. |
| 8,474,114 B2 | 7/2013 | Rolli |
| 8,518,005 B2 | 8/2013 | Handel et al. |
| 8,574,210 B2 | 11/2013 | Van Ingelgem et al. |
| 8,684,987 B2 | 4/2014 | Hasse et al. |
| 8,735,647 B2 | 5/2014 | Schoelling |
| 8,827,975 B2 | 9/2014 | Kimball et al. |
| 8,834,439 B2 | 9/2014 | Kimball et al. |
| 9,155,666 B2 | 10/2015 | Smet et al. |
| 9,622,919 B2 | 4/2017 | Pelley |
| 9,795,518 B2 | 10/2017 | Pelley |
| 2003/0176845 A1 | 9/2003 | Kollwitz |
| 2004/0199137 A1 | 10/2004 | Lamb et al. |
| 2004/0226152 A1 | 11/2004 | Prosise et al. |
| 2007/0234532 A1 | 10/2007 | Gilbert et al. |
| 2008/0065041 A1 | 3/2008 | Stan et al. |
| 2008/0119811 A1 | 5/2008 | Gilbert et al. |
| 2008/0275417 A1 | 11/2008 | Gilbert et al. |
| 2009/0082712 A1 | 3/2009 | Hasse et al. |
| 2010/0102481 A1 | 4/2010 | Hubbard, Jr. et al. |
| 2013/0018342 A1 | 1/2013 | Schmidt-Forst |
| 2013/0072892 A1 | 3/2013 | Hasse et al. |
| 2014/0000628 A1 | 1/2014 | Avery, Jr. et al. |
| 2014/0265026 A1 | 9/2014 | Schoelling |
| 2017/0172811 A1 | 6/2017 | Pelley |

FOREIGN PATENT DOCUMENTS

| | | |
|---|---|---|
| EP | 1547555 A | 6/2005 |
| EP | 1622556 B | 2/2006 |
| EP | 1759678 A | 3/2007 |
| EP | 1485054 B | 8/2007 |
| EP | 1622557 B | 11/2007 |
| EP | 1485055 B | 12/2007 |
| EP | 1601322 B | 12/2008 |
| EP | 1267782 B | 1/2012 |
| EP | 1485053 B | 10/2012 |
| EP | 2349158 B | 7/2013 |
| EP | 2712594 B | 9/2015 |
| EP | 2712596 B | 8/2016 |
| EP | 2900467 B | 6/2017 |
| EP | 2712595 B | 7/2017 |
| FR | 1178560 A | 5/1959 |
| WO | WO 1996/033682 A | 10/1996 |
| WO | WO 2004/080362 A | 9/2004 |
| WO | WO 2004/100846 A | 11/2004 |
| WO | WO 2004/100847 A | 11/2004 |
| WO | WO 2005/046548 A | 5/2005 |
| WO | WO 2005/046549 A | 5/2005 |
| WO | WO 2008/056339 A | 5/2008 |
| WO | WO 2009/040737 A | 4/2009 |
| WO | WO 2014/004798 A | 1/2014 |

APPARATUS FOR FORMING A CATAMENIAL TAMPON

CROSS-REFERENCE TO RELATED APPLICATIONS

This application claims the benefit of U.S. Provisional application 62/907,190 filed on Sep. 27, 2019, the complete disclosure of which is hereby incorporated herein by reference for all purposes.

FIELD OF THE INVENTION

The present invention relates to an intravaginal tampon for feminine hygiene. In particular, it relates to a doming tool for producing such tampon having a plurality of stations; and to the tampons made therewith.

BACKGROUND OF THE INVENTION

Intravaginal tampons have been used for decades. Two types of tampons are present on the market, digital tampons and tampons requiring an applicator. Typically, digital tampons are formed by radial compression of a blank with a set of jaws while applicator tampons are formed by moulding a blank. Both types of tampons have generally a cylindrical shape, and both have advantages and disadvantages.

Digital tampon can be inserted manually without an applicator, they have a neat smooth surface; however, the compression column created by the press jaw within the product to generate the rigidity required for digital insertion may be uncomfortable for some consumers. Applicator tampons may not have this rigidity issue; however they require the use of an applicator and generate additional waste.

It is also important to consider that a tampon may change in position while in place depending on the activity of the wearer, e.g. moving, doing sports or even coughing. This can create discomfort and even leakage if the new position of the tampon is not adapted.

Leakage avoidance and wearing comfort are two important benefits for the consumer.

Shaped tampons have been proposed to fulfill these requirements. These existing shaped products are claimed to match more precisely the wearer anatomy and thus provide a better protection against by pass leakage, reduce discomfort and generally stay in place more efficiently within the vagina.

EP2349158B1 by the Procter & Gamble Company purport to disclose a carrier mold having prongs that produces shaped tampons. When subjected to pressure by a pushrod the prongs of the carrier mold flex to substantially or partially open one end of the carrier mold.

EP1485055B1 by the Procter & Gamble Company purport to disclose a method for producing a shaped tampon. The method includes the following steps: providing a mold; a tampon pledget; transferring the tampon pledget into the mold using a transfer member resulting in a tampon mold; self-sustaining the shaped tampon wherein the shaped tampon has an undercut; and removing the shaped tampon from the tampon mold.

EP1267782B1 by the Procter & Gamble Company purport to disclose digital tampons which are capable of radially expanding into a non-circular cross-sectional shape upon exposure to a wet environment so as to reduce bypass leakage; the disclosure also relates to tampon blanks and a process of producing the tampons.

EP1759678A1 by Ontex Hygieneartikel Deutschland purport to disclose a tampon comprising at least three ribs defined by grooves, characterised in that at least one rib or groove, in transverse cross-section, has a median at least partially diverging from the radius and to a process for manufacturing tampon; the disclosure also relates to a press for manufacturing said tampon.

U.S. Pat. No. 9,155,666B2 by Ontex Hygieneartikel Deutschland purport to disclose a press for manufacturing a tampon, comprising at least three press jaws, whereby there is provided a penetrating segment, PSLG, configured to penetrate the absorbing material with a longitudinal groove, and penetrating segments, PSSG, configured to penetrate the absorbing material with a plurality of side grooves that are arranged in the longitudinal direction.

EP2712596B1 by Johnson & Johnson purport to disclose an intravaginal tampon for feminine hygiene and a method for producing said tampon having relatively deep, penetrating grooves in which adjacent penetrating jaws pass through the same tampon press space during manufacture and to an apparatus useful in making said tampon.

While the above examples describe presses to produce tampon with different profiles or grooves configuration, these tampons have traditional cylindrical shapes.

Further the above examples fail to provide indications about the doming tool configuration required to achieve a tampon with a complex longitudinal or radial shape.

SUMMARY OF THE INVENTION

It has been discovered that a shaped tampon with a shaped longitudinal profile and an elliptical cross section on at least a part of its length can provide a better fit to the wearer anatomy and thus increases the wearer comfort without compromising the fluid abortion properties.

In one aspect the present invention discloses a doming tool for manufacturing absorbent tampon. Said tool comprises a plurality of stations made of devices for shaping a tampon pledget tip, and a hollow mandrel engaging with the stations; the stations are supported by at least one mounting plate.

Furthermore, the said plurality of stations comprises at least one passive cavity and at least one chuck style device. The said hollow mandrel is a prismatic tube containing a movable sliding insert, wherein the hollow mandrel and the movable sliding insert support the tampon withdrawal end and partially the tampon lateral flank while the tampon tip is being shaped. The said sliding insert can move along the length of said hollow mandrel.

In another aspect the present invention relates to a method for shaping the insertion tip of an absorbent tampon pledget comprising the steps of: inserting a compressed tampon pledget in a hollow mandrel equipped with a sliding insert; contacting the tip of said tampon pledget to a first passive cavity doming tool to seal the tip of the tampon; contacting the tip of said tampon pledget to a first chuck style device; contacting the tip of said tampon pledget to a second chuck style device, wherein the movable jaws of the second chuck style device are rotated by 45° compared to the movable jaws of the first chuck style device; contacting the tip of said tampon pledget to a second passive cavity doming tool, which cavity is seamless; contacting the tip of said tampon pledget to a third passive cavity doming tool, which cavity is seamless and smaller than the cavity of said second passive cavity doming tool.

In yet another aspect, the present invention relates to shaped tampons obtained by a doming tool according to the present disclosure.

Other aspects and features of the present invention will become apparent in those ordinarily skilled in the art upon review of the following description of specific embodiments of the invention in conjunction with the accompanying drawings.

DETAILED DESCRIPTION OF THE PREFERRED EMBODIMENTS

As used in the specification and the claims, the term "pledget" and variants thereof relate to a pad or a compress of absorbent material such as fibers designed to absorb bodily fluids. A "tampon pledget", or "absorbent tampon pledget", relates to the compressed absorbent material after compression of a tampon blank in a press. The said tampon pledget has two extremities: an insertion tip and a withdrawal end; and a longitudinal axis passing through the said two extremities.

The present invention relates to a doming tool for absorbent tampon manufacture, said tool comprising a plurality of stations made of devices for shaping a tampon pledget tip, and a hollow mandrel engaging with the stations; said stations being supported by at least one mounting plate, wherein said plurality of stations comprises at least one passive cavity and at least one chuck style device. The hollow mandrel is a prismatic tube containing a movable sliding insert and said hollow mandrel and a movable sliding insert support the tampon withdrawal end and partially the tampon lateral flank while the tampon tip is being shaped. The sliding insert can move along the length of said hollow mandrel.

In a preferred embodiment, the tampon pledget tip interacts with all the stations of the said doming tool, in a sequence.

Preferably, the tip of the tampon pledget that is shaped is the insertion tip. The other end of the tampon pledget being the withdrawal end.

Figure 1:
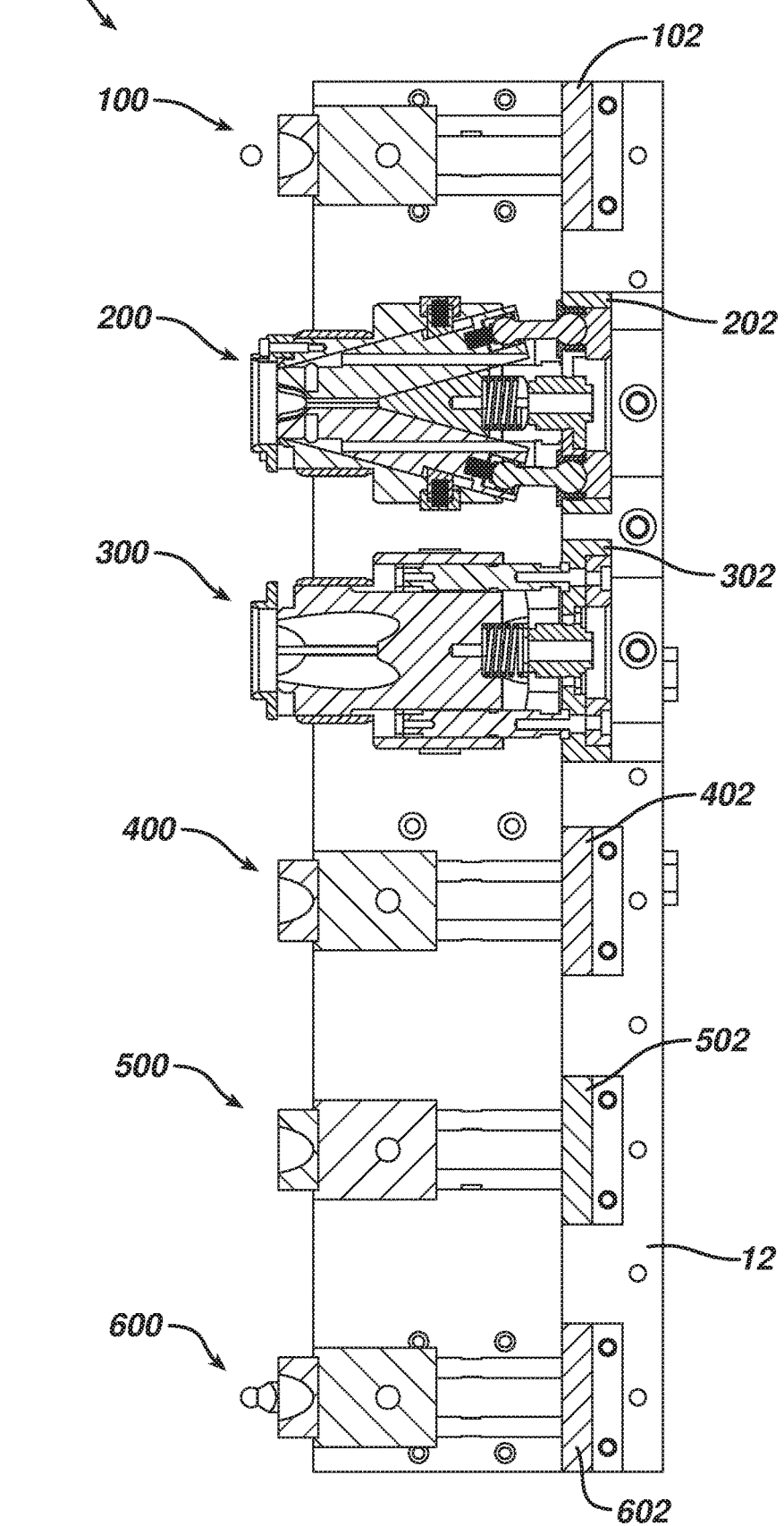
FIG. 1 is a cross-section an embodiment of the doming tool according to the present invention.
Figure 2:
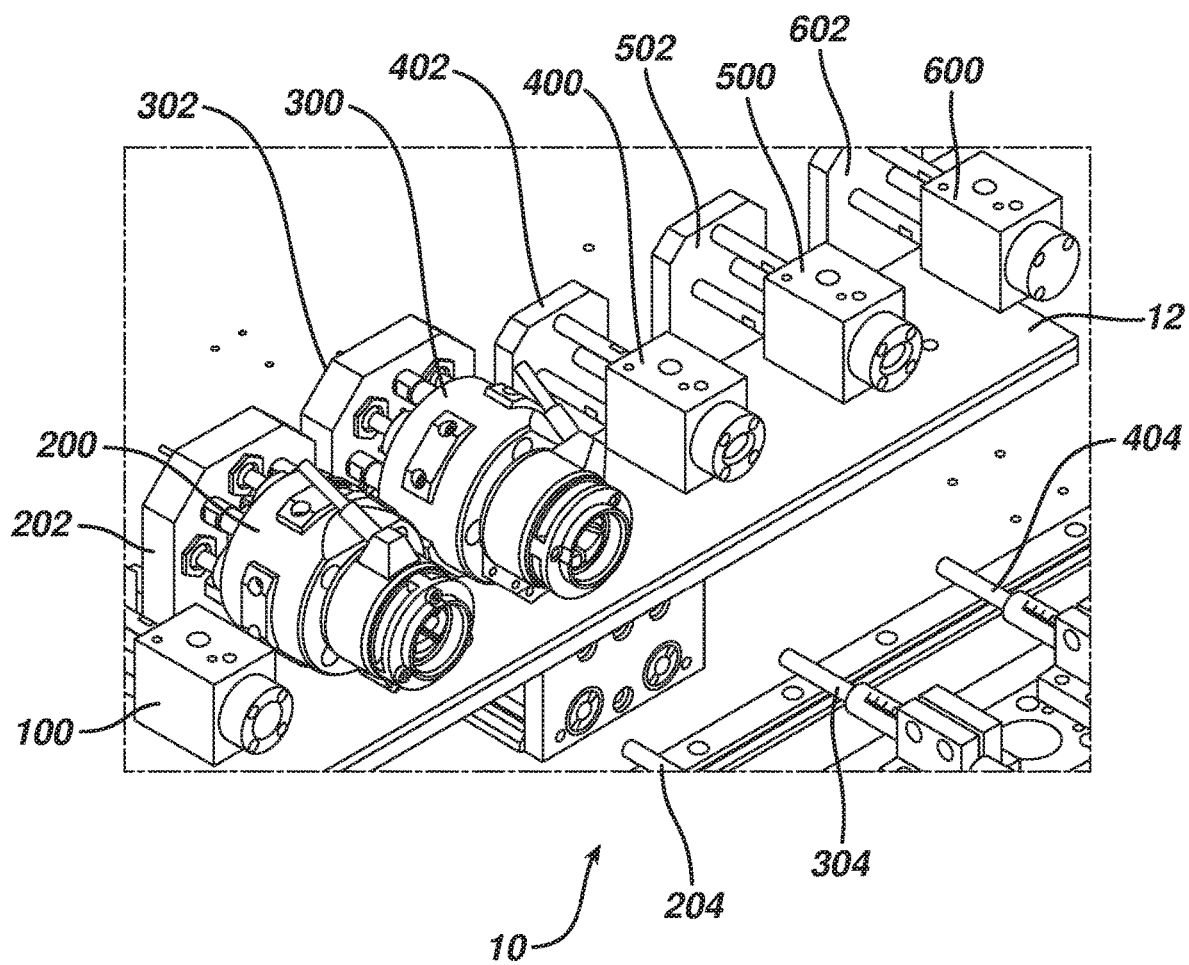
FIG. 2 is a perspective view of the embodiment disclosed in FIG. 1 in which the top of FIG. 1 corresponds to the left side of FIG. 2.

FIGS. 1 and 2 illustrate an example of the stations of a doming tool according to the present invention. In this embodiment the doming tool 10 comprises six stations 100, 200, 300, 400, 500, and 600, including three passive cavities 100, 400, and 500, and two chuck style devices 200 and 300. Each station is mounted on a plate, 102, 202, 302, 402, 502, and 602. The mounting plates 102-602 may be affixed to a rail 12.

Figure 3:
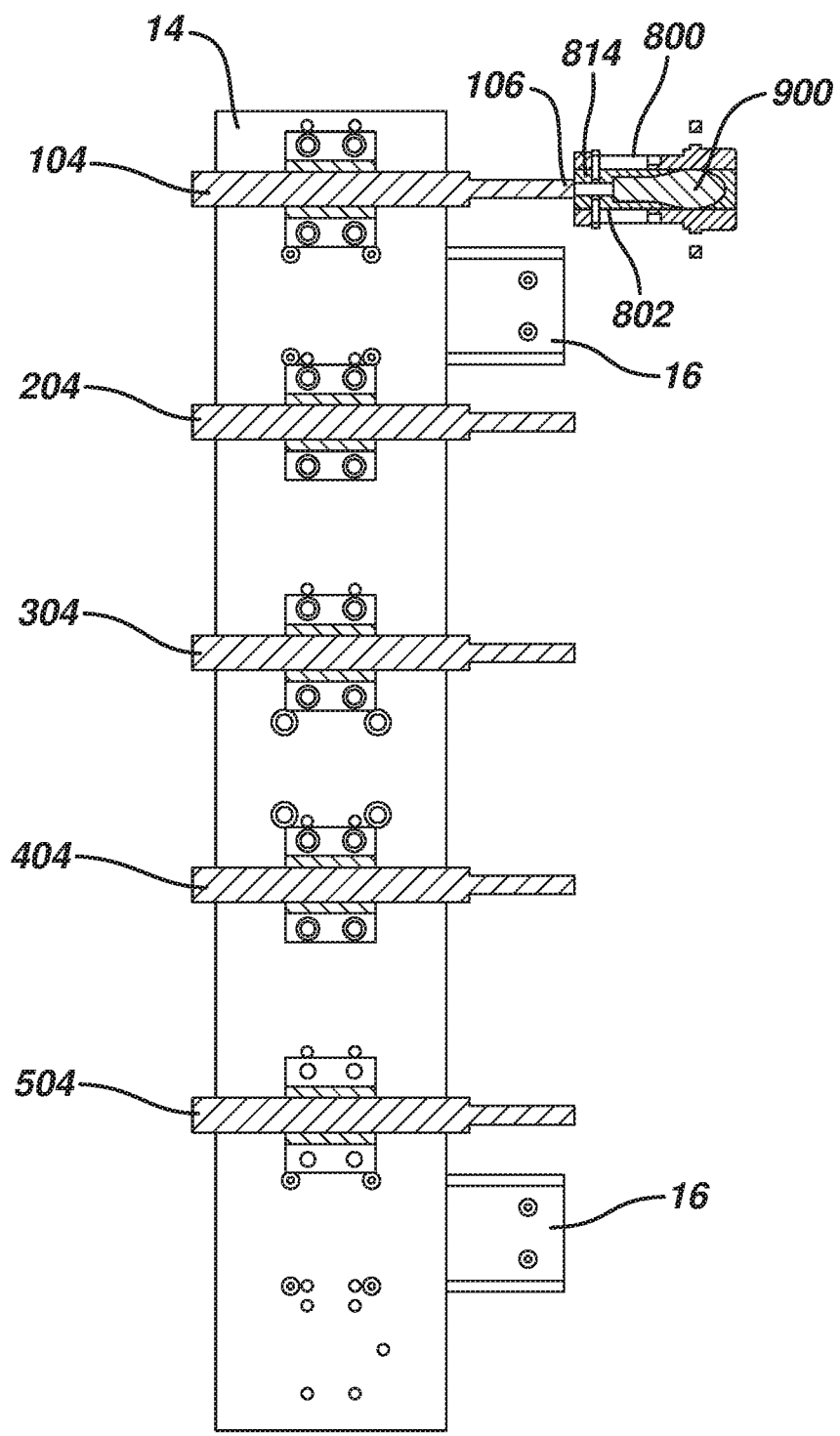
FIG. 3 is a top view of an embodiment of the plurality of push rods facing the doming tool stations. A representative tampon pledget is shown in a representative hollow mandrel in the upper right corner. As shown, the push rods are retracted, and the sliding insert is in a back position within the hollow mandrel.
Figure 4:
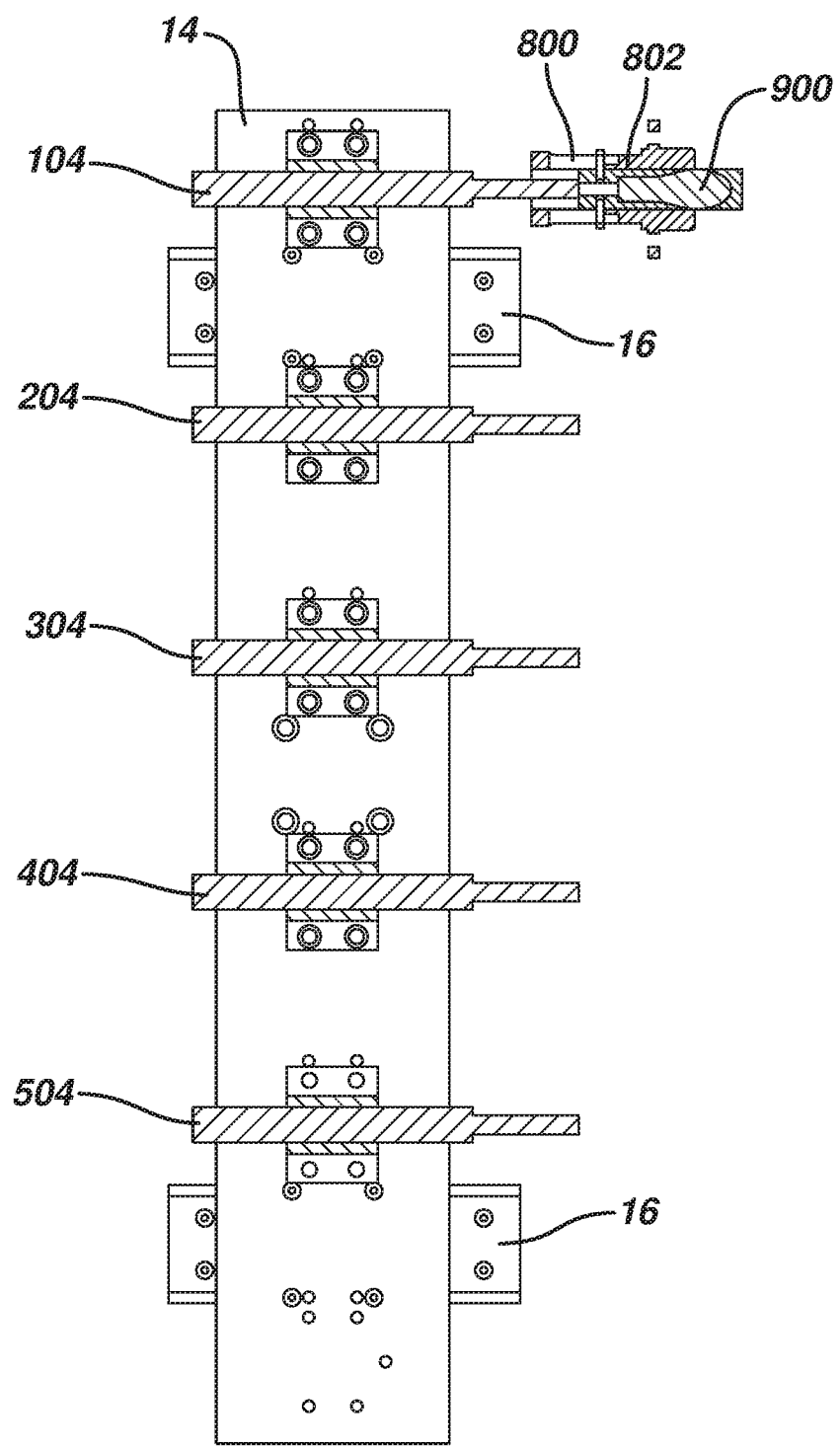
FIG. 4 is a top view of the embodiment of FIG. 3. As shown, the push rods are moved toward the stations of the doming tool, and the sliding insert is pushed in a forward position within the hollow mandrel.

FIGS. 3 and 4 illustrate an example of push rods 104, 204, 304, 404, and 504 mounted on a sliding push rod rail 14 that is in turn slidably mounted on a pair of brackets. A representative hollow mandrel 800 having a sliding insert 802 and an absorbent tampon prepared for a doming process are also represented.

While the above embodiments employ a plurality of stations mounted on a rail for linear operation, one of ordinary skill in the art will recognize that the stations could also be arranged and configured for rotary operation, such as using a drum, rotating disc, and the like.

As used in the specification and the claims, the term "prismatic tube" and variants thereof relate to a tube straight and with a constant cross-section.

In an embodiment of the present invention the said movable sliding insert 802 is sized such that it can slide freely within and along the length of the hollow mandrel 800 but is prevented from twisting or moving off axis by any significant amount. Preferably the said sliding insert 802 has a cross-section slightly smaller than the corresponding inner cross-section of the said hollow mandrel 800.

Figure 5:
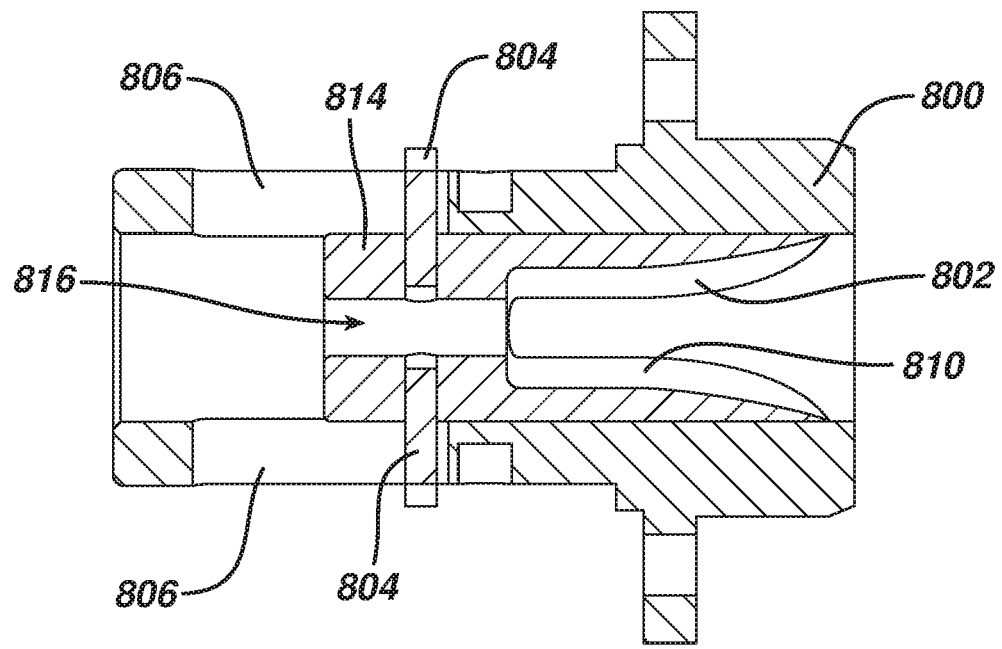
FIG. 5 is a cross-section view, along the longitudinal axis, of a hollow mandrel. As shown, the sliding insert is in a forward position within the hollow mandrel.
Figure 6:
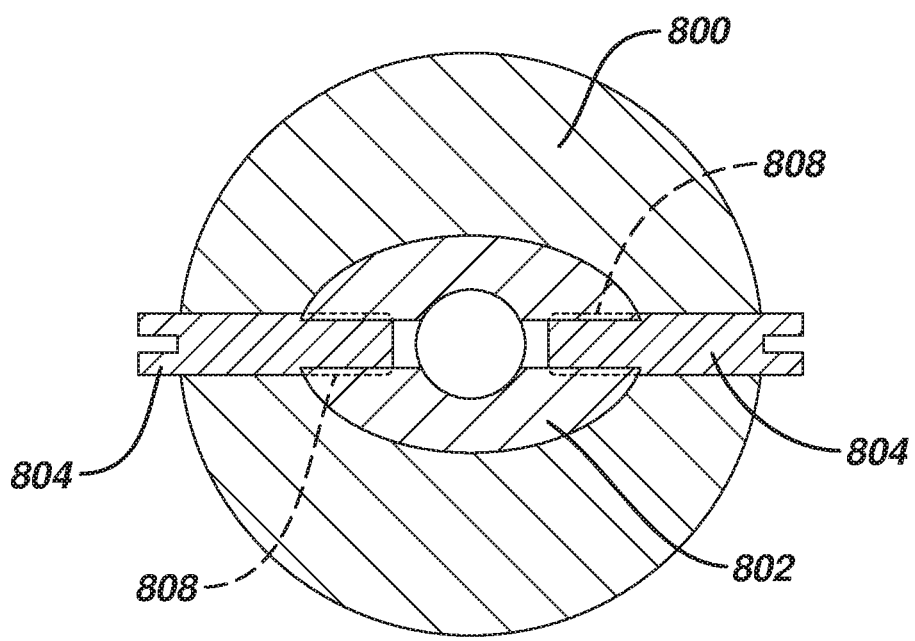
FIG. 6 is a cross section view, perpendicular to the longitudinal axis, of a hollow mandrel.
Figure 7A:
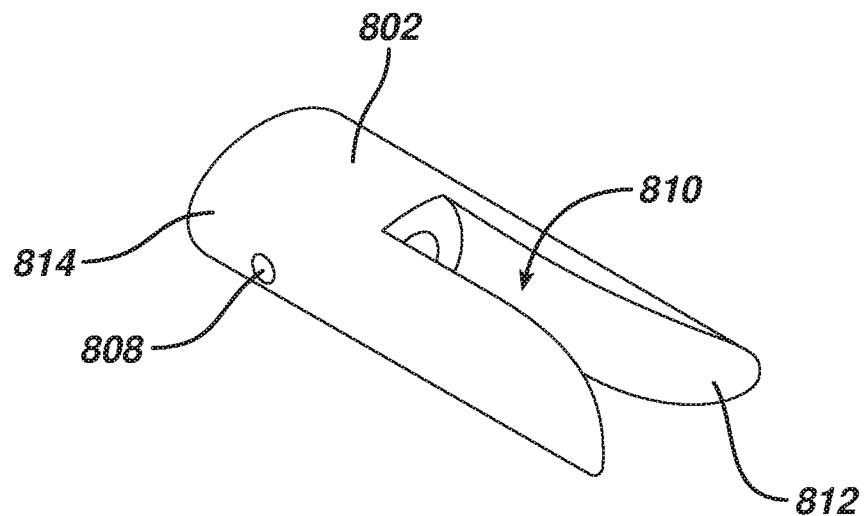
FIG. 7A is a perspective view of the sliding insert of FIGS. 5 and 6.
Figure 7B:
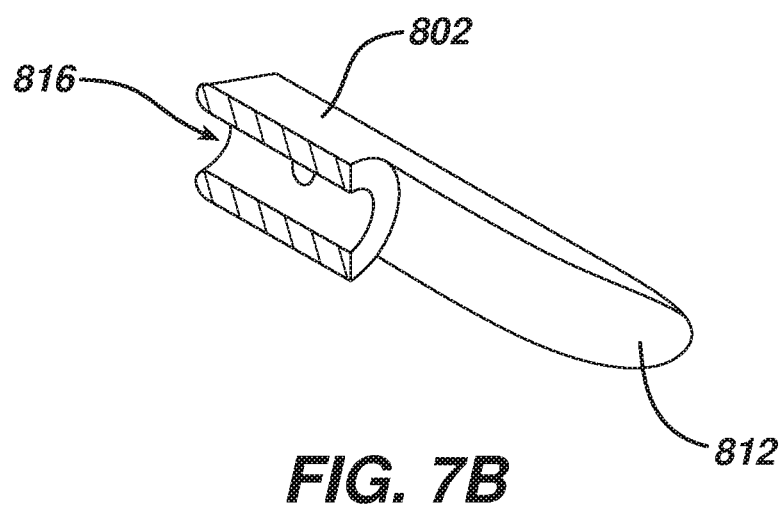
FIG. 7B is a cross-section of the perspective view of FIG. 7A.

FIGS. 5, 6 and 7 show a more detailed example of a hollow mandrel 800 and a sliding insert 802 according to the invention.

As used in the specification and the claims, the term "passive cavity" and variants thereof relate to a cavity that does not include any technical mean to change its volume or shape. The cavity has a fixed design and cannot be modified during the manufacturing. This type of cavity is different from the cavity of a chuck style devices which can change during the manufacturing due to the movable jaws.

The said mounting plate of the plurality station according to the present invention may be the same mounting plate for all stations, or for a group of stations, or a different mounting plate for each station.

Figure 8:
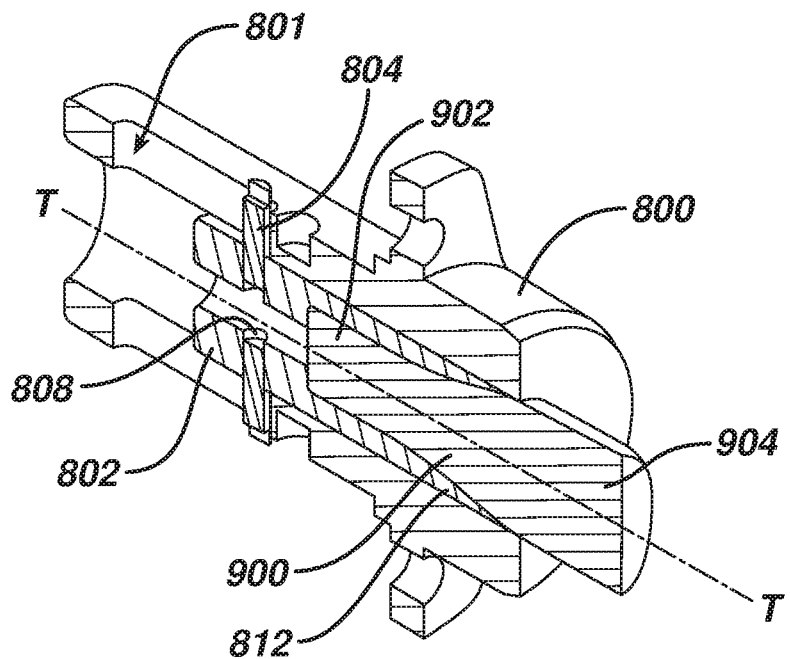
FIG. 8 is a cross-section of a perspective view, along the longitudinal axis, of a hollow mandrel of FIGS. 5-7 loaded with a shaped tampon in a forward position.

FIG. 8 illustrates a hollow mandrel 800 containing the sliding insert 802 and absorbent tampon 900 according to an embodiment of the present invention. The withdrawal end 902, insertion tip 904 (before doming), and longitudinal axis T-T of the tampon 900 and are indicated.

In a preferred embodiment, the doming tool 10 for absorbent tampon manufacture according to the present invention may comprise a sliding insert 802 that is provided with stop pins 804 which continuously engage with slots 806 in the said hollow mandrel 800 walls. This embodiment is desirable to limit the allowable displacement of the sliding insert 802 both forward and backward within the hollow mandrel 800.

Referring to FIGS. 5, 6 and 7; an embodiment of the hollow mandrel 800 and the sliding insert 802 are shown. The sliding insert 802 is equipped with stop pins 804 which are connected to holes 808 in the sliding insert walls. These stop pins 804 engage with slots 806 in the walls of the hollow mandrel 800.

In another embodiment, the present invention relates to a doming tool for manufacturing absorbent tampon wherein the said sliding insert may form a cup-shaped receptacle 810 sized for engaging with the tampon pledget 900 withdrawal end 902, and the rim 812 of the said receptacle 810 may be tapered and may engage with a portion of the tampon pledget lateral flank.

Figure 9:
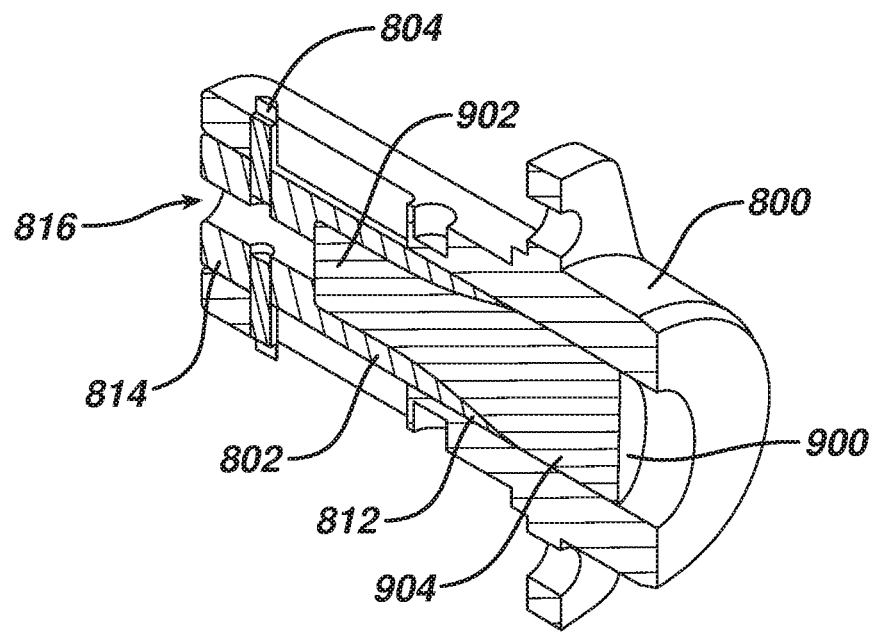
FIG. 9 is a cross-section of a perspective view, along the longitudinal axis, of a hollow mandrel of FIGS. 5-7 loaded with a shaped tampon in a rearward position.

FIGS. 5, 6 and 7; shows an example of cup shaped receptacle 810 and the tapered rim 812 of the sliding insert 802. FIGS. 8 and 9 show the sliding insert 802 with an absorbent tampon 900 and how the receptacle 810 of the sliding insert 802 engages the tampon withdrawal end 902.

As shown in FIG. 6, the outer shape of the said sliding insert 802 may also have an elliptical cross-section. In this embodiment the sliding insert 802 is movable in a cavity of the hollow mandrel 800, and said cavity has an elliptical cross-section, substantially matching that of the sliding insert 802.

As shown in FIGS. 5-7, the doming tool for absorbent tampon manufacture according to the present invention may also comprise a sliding insert 802 wherein the base 814 of said sliding insert 802 may have an aperture 816 through which a rod (not shown) can pass.

This embodiment is advantageous to remove the tampon pledget 900 from the hollow mandrel 800 and sliding insert 802 with a pushing device such as a rod for example.

In a preferred embodiment of the present invention relates to a doming tool for absorbent tampon manufacture according, wherein at least one of the said doming stations has a chuck style device including a rigid body having a plurality of movable jaws fitted in separate guideways. This chuck style device may further comprise that each movable jaw has a shaped cavity. The said movable jaws may further be disposed, preferably symmetrically, around the longitudinal axis of the said chuck style device, with an angle of 20° to 40° relative to said longitudinal axis.

As used in the specification and the claims, the term "Longitudinal axis of the chuck style device" and variants thereof relate to the axis of the chuck style device that is registered with the longitudinal axis of the tampon pledget.

In other words, the chuck style device according to the present invention may be a cylindrical rigid body comprising several movable jaws, each jaw having a shaped cavity. Furthermore, the jaws may be symmetrically disposed around a virtual conical surface having an included angle of between 20 and 40 degrees and said chuck style device is supported by a mounting plate.

Each jaw may be moved by an articulating ball-ended linkage fitting into the mating cavity at one end and connecting to a mounting plate. The jaws may open and close as a group when the rigid body is moved, respectively, forward (away from) and backwards (towards) relative to the mounting plate.

Figure 10:
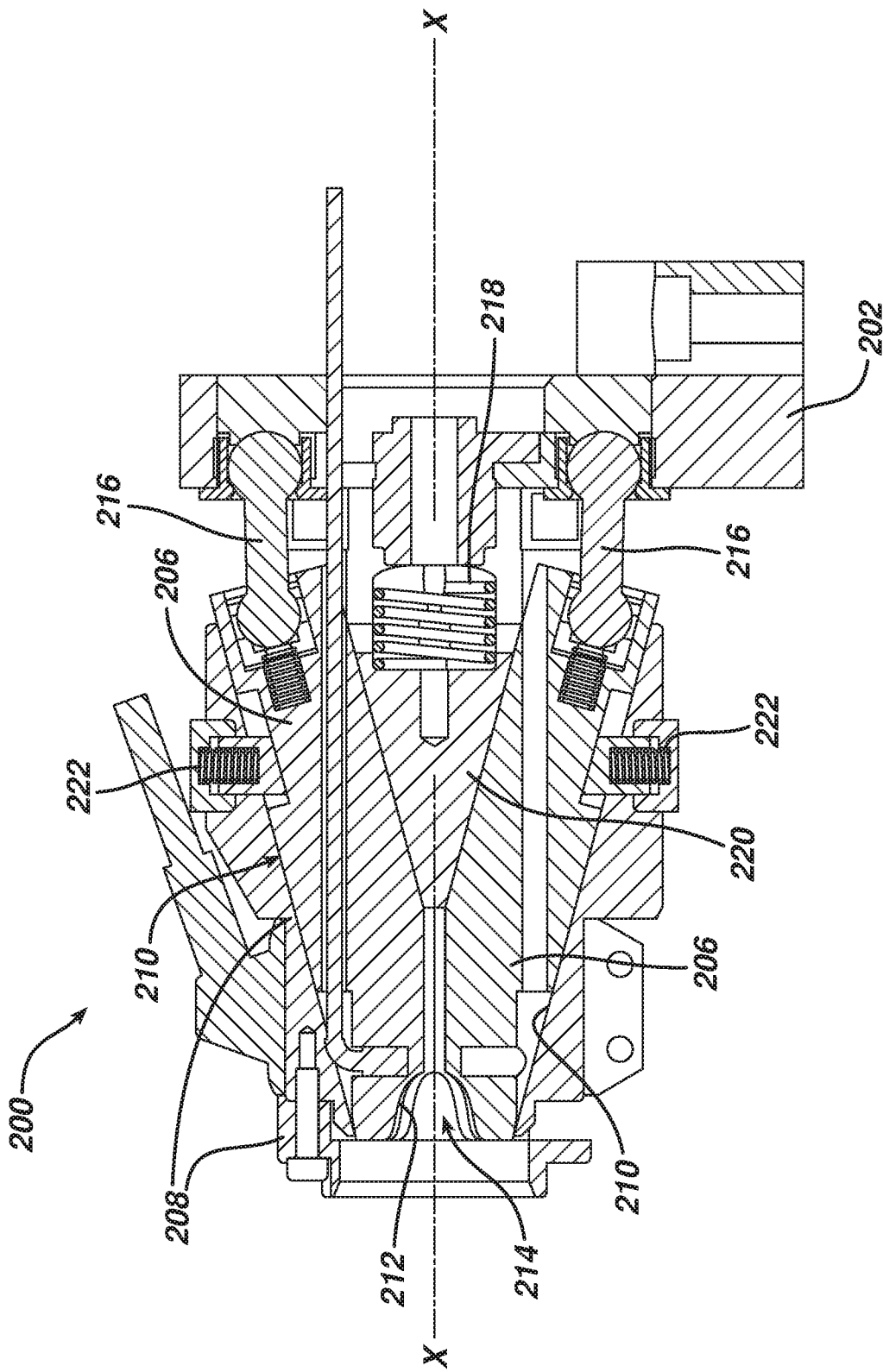
FIG. 10 is a cross-section, along the longitudinal axis, of a chuck style device for use in the doming tool of the present invention.
Figure 11:
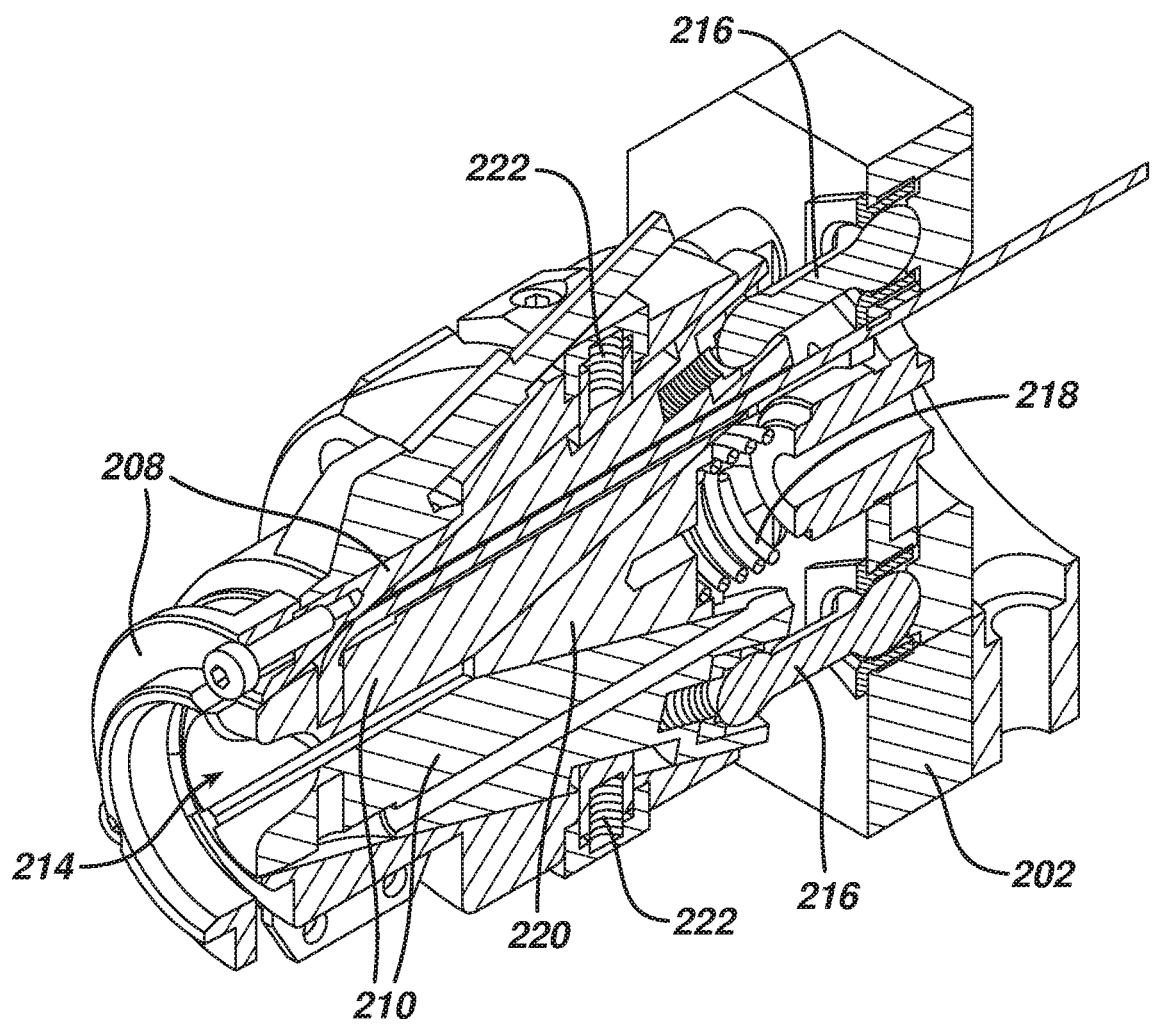
FIG. 11 is a cross-section of a perspective view of the device of FIG. 10.

Referring to FIGS. 10 and 11; an example of a chuck style device is illustrated. The chuck style device 200 comprises several movable jaws 206 fitted in guideways in the docking ring 208 of the said device. The outlines 210 of the said guideways are indicated. Each movable jaw 206 has a shaping profile 212 at one end and the combination of all the shaping profiles 212 creates the doming cavity 214. The longitudinal axis X-X of the chuck style device passes through the center of the doming cavity 214. Each moveable jaw 206 is mounted on a ball-end linkage 216, connecting the chuck style device 200 to its mounting plate 202. The movable jaws 206 are disposed about the longitudinal axis X-X of the chuck style device and define a virtual cone.

By "virtual cone," "virtual conical," and variants thereof, it is meant a shape that is conical or frusto-conical; for example, the tip of the cone may be truncated (frusto-conical), or portions of the sides of the cone may be flattened to create one or several planes.

In another embodiment, the doming tool for absorbent tampon manufacture according to the present invention, may comprise a chuck style device which is maintained in an open position by a compression spring until said chuck style device is actuated to a closed position by said hollow mandrel pushing the said rigid body toward the mounting plate.

In other words, the movable jaws of the chuck style device may be actuated by the pressure of hollow mandrel. The sliding insert may be in a back, or forward, position within the hollow mandrel when the hollow mandrel gets in contact with the chuck style device.

Thus, the movable jaws of the chuck style device may close on the insertion tip of the tampon pledget; or as an alternative, the insertion tip of the tampon pledget may be pushed toward the closed movable jaws of the chuck style device.

The compression spring 218 is illustrated on FIGS. 10 and 11. The compression spring 218 pushes a wedge 220 having a virtual conical shape away from the mounting plate 202; in reaction the movable jaws 206 slide in their guideways away from the device longitudinal axis X-X and thus open the doming cavity 214.

When a hollow mandrel pushes on the docking ring 208 to displace it toward the mounting plate 202, the lateral springs 222 apply a radial pressure, toward the longitudinal axis X-X, on the movable jaws 206 and thus on the wedge 220. The wedge 220 is forced toward the mounting plate 202, compressing the compression spring 218. As the movable jaws 206 are displaced toward the longitudinal axis X-X, the doming cavity 214 closes.

In other words, when a hollow mandrel 800 applies a pressure on a chuck style device 200, 300, the docking ring 208 and the wedge 220 are displaced toward the mounting plate 202, and the movable jaws 206 are displaced toward the longitudinal axis X-X.

Figure 12:
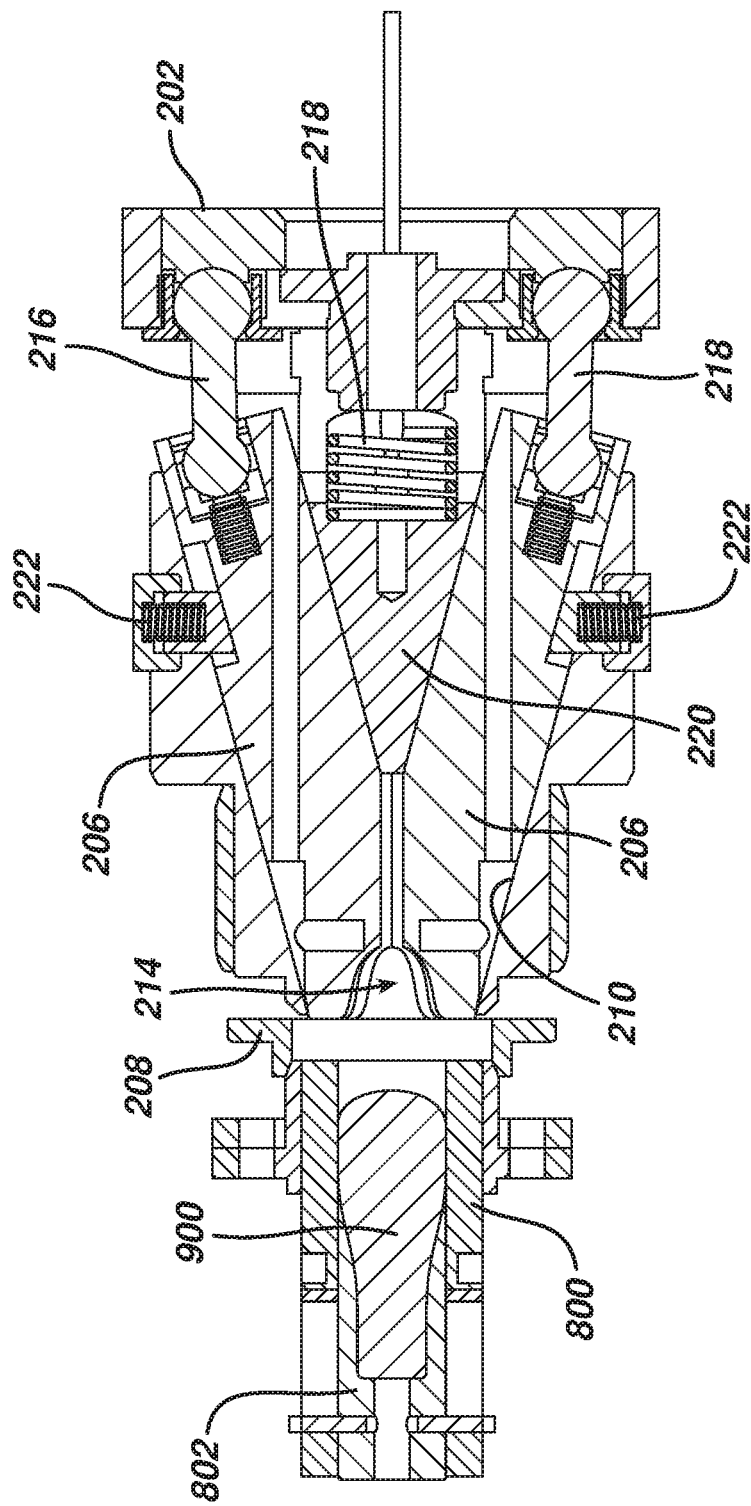
FIG. 12 is a cross-section, along the longitudinal axis, of a chuck style device interacting with a hollow mandrel loaded with a shaped tampon. As shown, the chuck style device jaws are in an open position.
Figure 13:
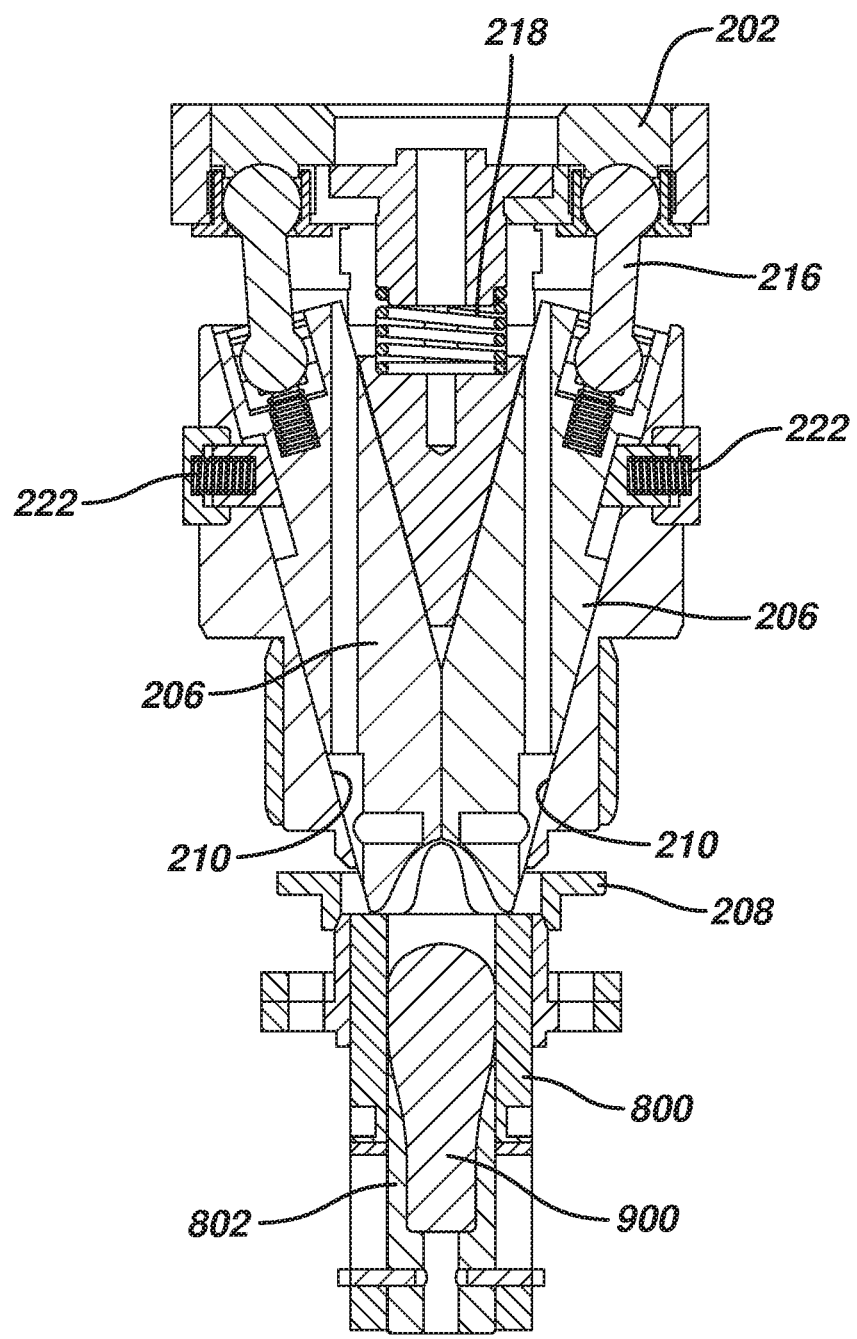
FIG. 13 is a cross section view, along the longitudinal axis, of the chuck style device of FIG. 12 interacting with a hollow mandrel loaded with a shaped tampon. As shown, the chuck style device jaws are in a closed position.
Figure 14:
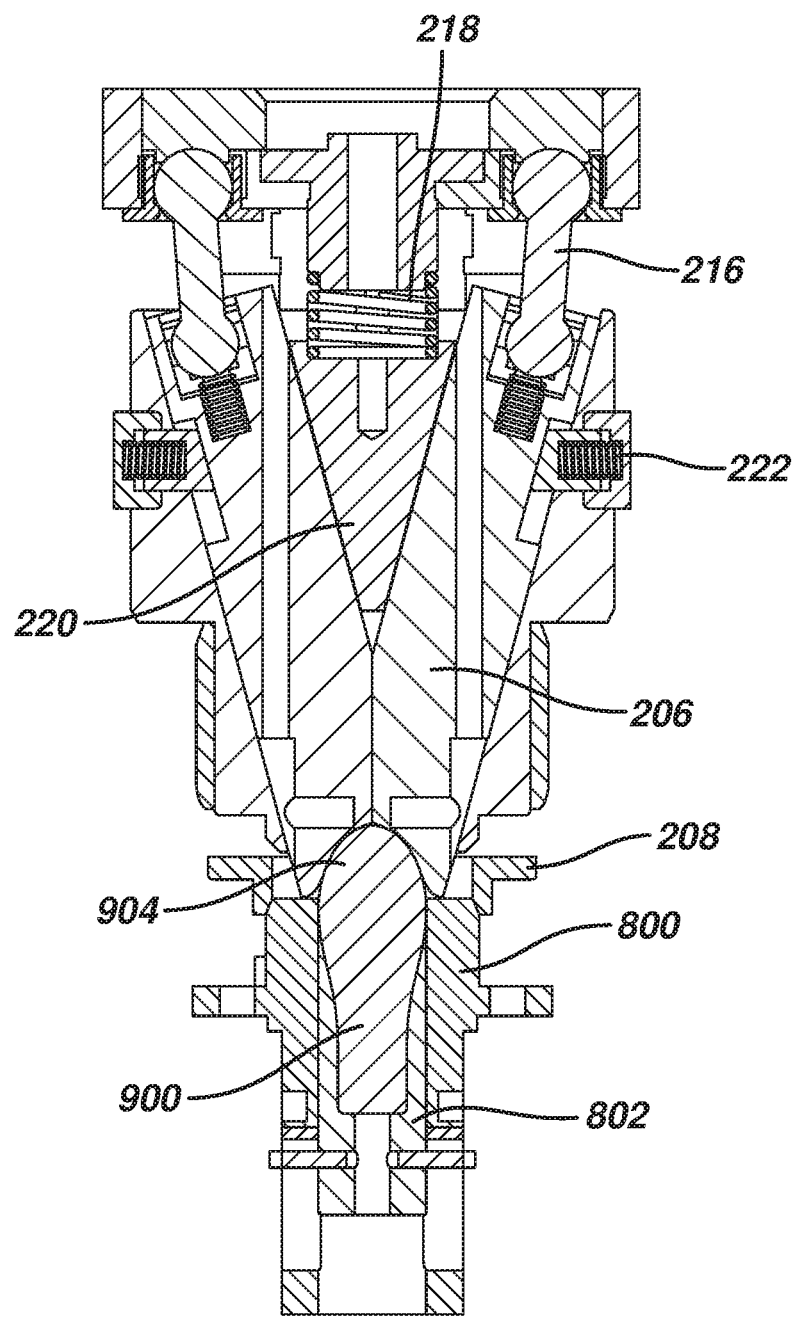
FIG. 14 is a cross-section, along the longitudinal axis, of the chuck style device of FIGS. 12 and 13 interacting with a hollow mandrel loaded with a shaped tampon As shown, the chuck style device jaws are in a closed position and in contact with the insertion tip of the shaped tampon.
Figure 15:
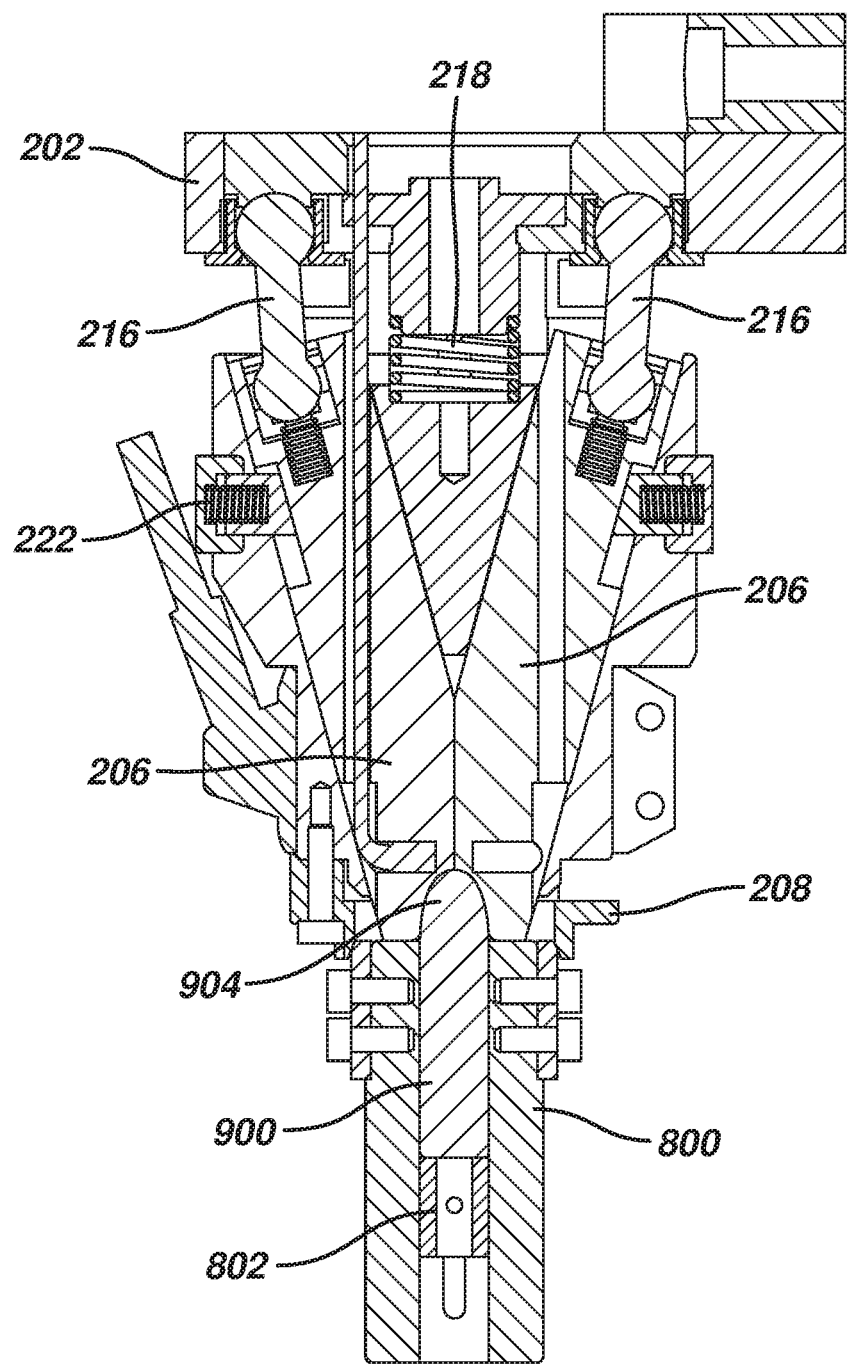
FIG. 15 is a cross-section, along the longitudinal axis, of the configuration disclosed in FIG. 14, rotated by 90° rotation, about the longitudinal axis.

FIGS. 12 and 13 illustrate these changes in configuration. In FIG. 12 the hollow mandrel 800 is merely touching the docking ring 208 and is not applying sufficient force to displace either the docking ring 208 or wedge 220. Thus, the doming cavity 214 is in an open position. In FIG. 13, the hollow mandrel 800 is applying sufficient force to displace both the docking ring 208 and wedge 220. Thus, the doming cavity 214 is in a closed position before the absorbent tampon 900 (pre-domed) is pushed into the doming cavity 214. FIGS. 14 and 15 (showing a view of FIG. 14 rotated by 90° about the longitudinal axis X-X) illustrate the domed tampon 900 when the hollow mandrel 800 is fully engaged with the docking ring 208 to form the doming cavity 214 in the closed position.

The doming tool for absorbent tampon manufacture according to the present invention may also contain a chuck style device that is equipped with a temperature control mean. Said temperature control mean may be used to increase or decrease, and control, the temperature of the movable shaped cavity.

In a preferred embodiment, the doming tool for absorbent tampon manufacture according to the present invention has a plurality of stations that may comprise at least two chuck style devices, and each chuck style device may have a different set of movable jaws.

Having at least two chuck style devices with different cavities may be desirable as it allows to compress the tampon pledget insertion tip in at least two different ways, one after the other. For example, this embodiment allows a sequential formation of the shaped insertion dome to minimize the potential for artifacts of the junctions between adjacent the shaping profiles 212 in the doming cavity 214, thereby creating a neater surface on the insertion tip that is more appealing for the consumer.

In a particular embodiment of the present invention doming tool, comprising at least two chuck style devices, the movable jaws of the second chuck style device may be rotated around the longitudinal axis of said chuck style device when compared to the first chuck style device movable jaws.

Figure 16:
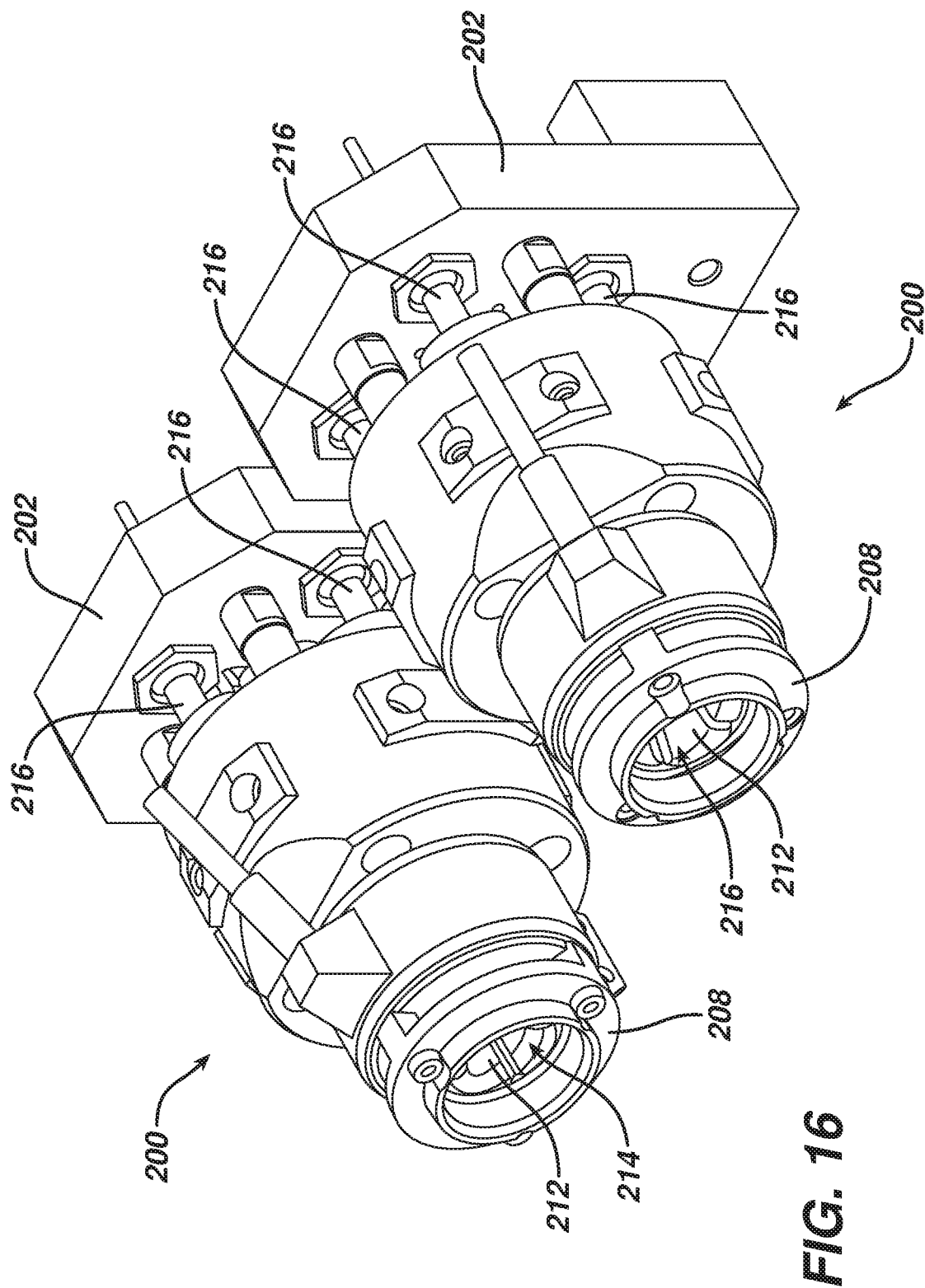
FIG. 16 is a perspective view of a pair of chuck style devices, one rotated by 45° about its longitudinal axis with respect to the other.

Preferably the rotation between first and second chuck style devices movable jaws, according to the longitudinal axis, is by 45°; this embodiment is illustrated on FIG. 16. The two chuck style devices are shown in which like reference numerals are as described above.

In another preferred embodiment, the doming tool for absorbent tampon manufacture according to the present invention has a plurality of stations that may comprise at least two, preferably three passive cavities.

As discussed above this plurality of passive cavities may be advantageous as it may create a more uniform, neater surface on the insertion tip of the tampon pledget.

One of the said passive cavities of the doming tool may seal or otherwise smooth the insertion tip of the tampon, before the tip of the tampon is placed in contact with the doming cavity of a chuck style device.

Passive cavities of the doming tool may be seamless. A doming tool according to the peent invention may contain may comprise passive cavities wherein at least two of the said passive cavities are seamless cavities, and one of the said passive cavities is 10% smaller than the other.

In yet another embodiment the doming tool for absorbent tampon manufacture according to the present invention, the last station of said doming tool may be a return station, equipped with a shaped pusher which returns the tampon back inside the said hollow mandrel.

FIG. 1 illustrates an example of a return station 600 with a shaped pusher 604.

In a preferred embodiment, the doming tool for absorbent tampon manufacture according to the present invention comprises at least one station that may be equipped with a movable push rod to apply a pressure, along the longitudinal axis of the tampon pledget and toward the mounting plate, on the sliding insert base supporting the tampon pledget inside the said hollow mandrel.

Figure 17:
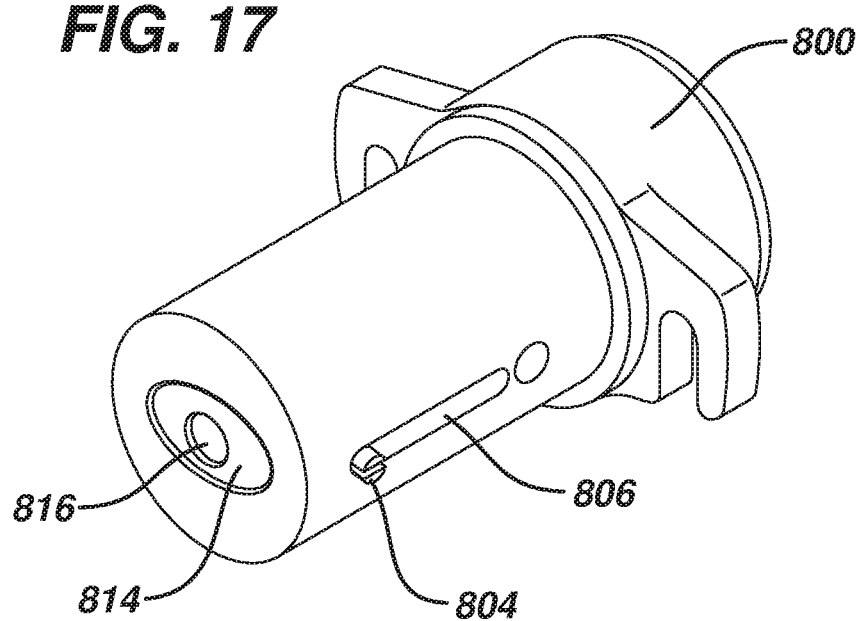
FIG. 17 is a perspective view of a hollow mandrel and a sliding insert according to the present invention in a first configuration.
Figure 18:
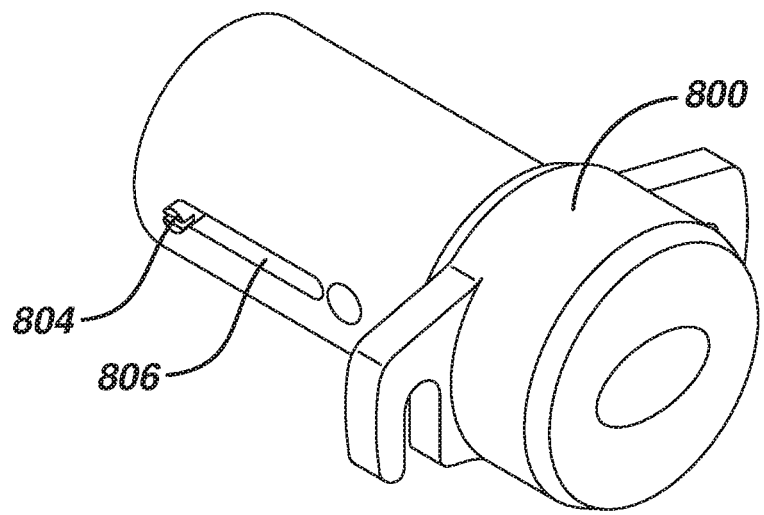
FIG. 18 is a perspective view of the hollow mandrel and sliding insert disclosed in FIG. 17, rotated by 90° about an axis perpendicular to its longitudinal axis.

FIGS. 5 and 17 show the sliding insert base 814 on which pressure is applied by the push rod. FIGS. 3 and 4 show an example where five stations are equipped with push rod 104, 204, 304, 404, and 504, and of a push rod end 106 in contact with the sliding insert base 814.

The said movable push rod acts as a counter pusher for the chuck style device, pressing the sliding insert 802 and thus the tampon pledget 900 insertion tip 904 towards the doming cavities 214, 314.

When applying the said pressure along the longitudinal axis of the tampon pledget and toward the mounting plate, it is preferred that the tampon is fully supported by the sliding insert and the hollow mandrel against the longitudinal and axial forces applied. This minimizes the likelihood of any deformation of the tampon during the dome shaping In other words, the absorbent tampon to be domed would be carried in a hollow mandrel with a sliding Insert, whereby the axial position and reactive force is determined by said push rod acting on the base of the sliding insert, or outer rear surface of the sliding insert. Thus, the extremity of the absorbent tampon opposite to that being domed is protected against damage.

Optionally, the doming tool may have more than one of stations equipped with a movable push rod and the said movable push rods have different lengths.

For example, this allows to compensation the fact that the tampon pledget will be shortened slightly by each successive tool station application. Thus, each station can be made to apply sufficient force to fully impart its intended shaping effect.

In an embodiment, the present invention relates to a doming tool for absorbent tampon manufacture, wherein less or equal to 30%, particularly 25%, preferably 20%, more preferably 15%, of the tampon total length starting from the tampon insertion tip, is engaged with at least one of the stations of the said doming tool.

By "tampon total length" it is meant the length according to the tampon pledget longitudinal axis.

Alternatively, the present invention relates to a doming tool, wherein more than 1%, particularly more than 5%, preferably more than 10% of the tampon total length starting from the tampon insertion tip, is engaged with at least one of the stations of the said doming tool.

In another embodiment, the doming tool for absorbent tampon manufacture according to the present invention, may have at least 70%, particularly at least 80%, preferably at least 85%, of the tampon total length starting from the tampon withdrawal end, that is in contact with the said sliding insert and hollow mandrel.

In other words, during the doming when a pressure is applied to the tampon toward the stations, at least 70%, particularly at least 80%, preferably at least 85%, of the tampon pledget surface is supported by the said sliding insert and hollow mandrel, for protection against deformation due to the forces that are applied. For example, a deformation may damage the compression column of a digital tampon and such a damaged digital tampon may be unusable by a consumer.

A method for shaping the insertion tip of an absorbent tampon using a doming tool according to the present invention may comprise the steps of: inserting a tampon pledget in a hollow mandrel equipped with a sliding insert, contacting the tip of said tampon pledget to a first passive cavity doming tool to seal the tip of the tampon, contacting the tip of said tampon pledget to a first chuck style device, contacting the tip of said tampon pledget to a second chuck style device, wherein the movable jaws of the second chuck style device are rotated by 45° compared to the movable jaws of the first chuck style device, contacting the tip of said tampon pledget to a second passive cavity doming tool, which cavity is seamless, and contacting the tip of said tampon pledget to a third passive cavity doming tool, which cavity is seamless and smaller than the cavity of said second passive cavity doming tool.

Preferably the movable jaws of the second chuck style device are rotated by 45° according to the longitudinal axis of the chuck style device. Said axis is registered with the tampon pledget longitudinal axis when the tampon is engaging with the chuck style device.

By "smaller than the cavity of said second passive cavity" it is meant that the volume of the cavity is smaller, or in another embodiment it could alternatively mean that the perimeter or the cavity rim is smaller.

In yet another embodiment, the invention may refer to an absorbent tampon which insertion tip may have been shaped using a doming tool as described in the present disclosure.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method for shaping the insertion tip of an absorbent tampon using a doming system comprising a plurality of stations made of devices for shaping a tampon pledget tip, and a hollow mandrel engaging with the stations; said stations being supported by at least one mounting plate, wherein said plurality of stations comprises at least one passive cavity and at least one chuck and wherein said hollow mandrel has a length and is a prismatic tube containing a movable sliding insert, and said hollow mandrel and movable sliding insert are arranged and configured to support a tampon withdrawal end and partially a tampon lateral flank while the tampon tip is being shaped during use of the doming system; and wherein said movable sliding insert can move along the length of said hollow mandrel; the method comprising the following steps:
    a) inserting a tampon pledget in the movable sliding insert of the hollow mandrel,
    b) contacting the tip of said tampon pledget to a first passive cavity doming tool of the doming system to seal the tip of the tampon,
    c) contacting the tip of said tampon pledget to a first chuck style comprising first chuck moveable jaws,
    d) contacting the tip of said tampon pledget to a second chuck style comprising second chuck moveable jaws, wherein the second chuck movable jaws are rotated by 45° with respect to the first chuck movable jaws,
    e) contacting the tip of said tampon pledget to a second passive cavity doming tool of the doming system, which cavity is seamless, and
    f) contacting the tip of said tampon pledget to a third passive cavity doming tool of the doming system, which cavity is seamless and smaller than the cavity of said second passive cavity doming tool of the doming system.

2. The method of claim 1, wherein the tampon pledget has a length extending from the tampon insertion tip and each step of contacting the tip of said tampon pledget to the first or second passive cavity doming tools or contacting the tip of said tampon pledget to the first or second chucks comprises contacting at most 30% of the tampon length thereto.

3. The method of claim 2, wherein each step of contacting the tip of said tampon pledget to the first or second passive cavity doming tools or contacting the tip of said tampon pledget to the first or second chucks comprises contacting at most 25% of the tampon length thereto.

4. The method of claim 3, wherein each step of contacting the tip of said tampon pledget to the first or second passive cavity doming tools or contacting the tip of said tampon pledget to the first or second chucks comprises contacting at most 20% of the tampon length thereto.

5. The method of claim 4, wherein each step of contacting the tip of said tampon pledget to the first or second passive cavity doming tools or contacting the tip of said tampon pledget to the first or second chucks comprises contacting at most 15% of the tampon length thereto.

6. The method of claim 2, wherein at least 70% of the tampon length starting from the tampon end opposite the tampon insertion tip, is in contact with the said movable sliding insert and hollow mandrel.

7. The method of claim 6, wherein at least 80% of the tampon length starting from the tampon end opposite the tampon insertion tip, is in contact with the said movable sliding insert and hollow mandrel.

8. The method of claim 7, wherein at least 85% of the tampon length starting from the tampon end opposite the tampon insertion tip, is in contact with the said movable sliding insert and hollow mandrel.

* * * * *